United States Patent [19]

Cottone, Sr. et al.

[11] Patent Number: 5,509,911
[45] Date of Patent: Apr. 23, 1996

[54] ROTATING ADAPTER FOR A CATHETERIZATION SYSTEM

[75] Inventors: Joseph R. Cottone, Sr., Marietta; Anthony J. Cottone, Ball Ground, both of Ga.

[73] Assignee: Maxxim Medical, Inc., Sugar Lane, Tex.

[21] Appl. No.: 982,498

[22] Filed: Nov. 27, 1992

[51] Int. Cl.⁶ .................................................. A61M 25/00
[52] U.S. Cl. ........................ 604/283; 604/905; 285/315; 285/322
[58] Field of Search .......................... 604/29, 283, 905; 285/305, 313, 315, 322

[56] References Cited

U.S. PATENT DOCUMENTS

| | | | |
|---|---|---|---|
| 2,893,395 | 7/1959 | Buck | 128/349 |
| 3,503,385 | 3/1970 | Stevens | 128/2 |
| 3,785,683 | 1/1974 | Adelhed | 285/169 |
| 4,152,017 | 5/1979 | Abramson | 285/260 |
| 4,254,773 | 3/1981 | Waldbillig . | |
| 4,398,757 | 8/1983 | Floyd et al. | 285/315 |
| 4,451,069 | 5/1984 | Melone | 285/86 |
| 4,834,149 | 5/1989 | Fournier et al. | 141/1 |
| 4,857,062 | 8/1989 | Russell | 604/256 |
| 4,895,570 | 1/1990 | Larkin | 604/411 |
| 4,932,114 | 6/1990 | Morse et al. | 29/443 |
| 5,137,524 | 8/1992 | Lynn et al. | 604/283 |
| 5,141,263 | 8/1992 | Vorden | 285/314 |
| 5,284,134 | 2/1994 | Vaughn et al. | 128/200.24 |

*Primary Examiner*—Corrine Maglione
*Attorney, Agent, or Firm*—Veal & Marsh

[57] ABSTRACT

A rotating adapter for connecting two tubular fluid carrying members in a catheterization system. The adapter (10) includes a standard threaded Luer connector at one end (28) for connection to a flexible catheter, and is rotatably affixed about a stem (22) at its other end. The adapter includes a temporarily expansible collar (40) for engaging with a shoulder (52) on the stem (22) in a snap fit. The shoulder (52) engages an annular rim or undercut (65) located on the interior wall of the collar (40). Notches provided in collar (40) permit the collar to temporarily expand radially to receive the stem, and the collar snaps around the shoulder when the stem is inserted into the shoulder. A tubular reinforcer ring (14) slidably interfits over the collar after the stem is fully inserted into the collar and engages the undercut, thereby resisting radial expansion of the collar during pressurization. The entire rotating adapter is made of injection molded plastic and can be assembled quickly and efficiently by hand, without any special tools for permanently deforming the collar.

30 Claims, 5 Drawing Sheets

ROTATING ADAPTER FOR A CATHETERIZATION SYSTEM

TECHNICAL FIELD

The present invention relates to rotatably connecting one fluid carrying member to another fluid carrying member, and more particularly relates to a rotating adapter for connecting a catheter to a fluid reservoir in a catheterization system such that the catheter can rotate about the longitudinal axis of the adapter.

BACKGROUND OF THE INVENTION

Many technical fields require interconnection of two tubular members such that one of the members is rotatable about the longitudinal axis of the interconnected members. Rotating adapters or fittings are used to provide a rotatable connection between the tubular members, for example, between a rotatable member and a tubular stem. Sometimes, these members carry pressurized fluid, which necessitates sealed connections between the members and the adapter.

Rotating adapters are often used in medical catheterization systems, where tubular catheters are inserted into the body of a patient to remove or introduce fluid. For example, medical personnel sometimes are required to insert a flexible tubular catheter into a blood vessel during surgery, or into the bladder to remove fluids. Such applications require that the flexible catheter be rotatable relative to a stationary fluid carrying manifold, so as to facilitate movement of the catheter into and through the patient's body. The manifold, which typically includes a tubular stem for attachment of the catheter, is then connected to a fluid reservoir located outside the patient's body which serves as a supply of fluid to be injected into the patient, or as a reservoir for fluid withdrawn from the patient. Use of rotatable adapters allows fluid passage while still permitting the required rotation of the catheter relative to the stem during catheter insertion or removal.

Recently, disposable plastic catheterization system adapters have become popular for use in medical catheterization systems. Disposable products avoid problems associated with sterilization of reusable catheterization system parts made of metal. However, some designs of disposable plastic adapters are subject to failure when used with pressurized fluids. Furthermore, some designs require injection molds that include expensive collapsible core pins to remove the molded parts. Moreover, prior art approaches to improving the pressure handling characteristics have increased the complexity and expense of manufacture of disposable catheterization system parts.

For example, the two-piece swivel coupling adapter described in U.S. Pat. No. 4,254,773 to Waldbillig has a flexible lip which snaps over a tapered flange to rotatably connect the adapter and a catheter. The tapered flange is only captured by a thin flexible inwardly directed plastic lip having a recess or undercut for engaging with the flange in a snap fit. At least partially because the plastic lip is not reinforced, this catheterization system is subject to leakage at higher pressurizations of fluid in the catheter.

Although the Waldbillig device is fairly simple to assemble (only a snap-fit is required), its susceptibility to pressure failures makes it undesirable in applications involving higher pressure fluids (the device has only been tested to 700 psi). Moreover, the injection molds for making the inwardly directed lip for capturing the flange likely requires provision of a collapsible core pin in the mold, so that the undercut or inwardly formed recess in the lip can be removed from the mold. This adds to the cost of the injection mold.

One approach to a catheterization system adapter that offers improved pressure handling characteristics is described in U.S. Pat. No. 4,932,114 to Morse. This rotating adapter comprises two plastic pieces that assemble to form a swivel coupling apparatus. To assemble the device, the adapter is mated with a manifold stem such that a ring on the adapter extends beyond a shoulder on the stem. The adapter ring is then rotated on a forming wheel and heated by a heating device to soften the plastic and permanently deform the plastic ring about the shoulder. While this approach offers greater pressure carrying capability, ostensibly operative at pressures up to 1600 psi, expensive equipment is required to affix the adapter to the catheter stem and permanently deform the ring. Thus, adapters made in accordance with this patent are more difficult to fabricate (simple hand assembly is not possible) and thus more expensive.

Accordingly, there is a need for a low cost rotatable adapter that is more pressure resistant than prior art designs, is easy to assemble manually, and does not require special equipment for either manufacturing the injection molded parts or deforming the parts permanently with expensive heating equipment after assembly.

SUMMARY OF THE INVENTION

The present invention solves the above-identified problems in the art by providing an improved rotating adapter that is easy to manufacture and assemble, requires no special molds or forming equipment, and is able to withstand increased pressures. Briefly described, the present invention of a rotating adapter comprises expansion means for enabling temporary radial expansion of the adapter to permit the stem of a catheterization system to be inserted into the adapter, means for securely capturing the adapter on the stem, and reinforcer means for resisting radial expansion of the adapter after the stem and the adapter have been mated. The preferred expansion means comprises at least one notch formed into a collar on the adapter. The notch facilitates outward radial expansion of the distal end of the adapter's collar during mating of the adapter to the stem. The preferred capture means comprises an undercut in the material of the collar of the adapter. The undercut engages the shoulder of the stem when the adapter and stem are mated. The preferred reinforcer means comprises a tubular reinforcer ring that slidably interfits over the adapter collar to prevent outward radial motion of the collar. The ring resists the tendency of the undercut to disengage from the shoulder on the stem, and provides additional pressure containment.

The preferred embodiment of the invention is particularly suitable for use in medical applications involving catheterization systems that include fluid distribution manifolds having one or more elongate stems connecting to the manifold and distributing or collecting pressurized fluids. In accordance with the invention, these stems are provided with an outer tubular section and an inner tubular section, where the diameter of the outer section is greater than the diameter of the inner section, thereby defining a shoulder at the juncture of the outer section and the inner section. The rotatable adapter rotatably interfits with the stem and maintains pressure in the catheterization system.

More particularly described, the preferred adapter comprises a first injection molded piece comprising a threaded Luer receptacle at one end, at least one fin for grasping, and a stem-receiving collar at the other end for mating with a manifold stem. The fins facilitate attachment of the adapter to threaded Luer connections or rotation of a catheter connected to the adapter. The stem-receiving collar is provided on one end of the adapter, opposite the grasping fins. An "O" ring gasket is inserted between the stem and an interior shoulder formed inside the collar prior to assembly. The collar includes an annular rim around an outermost or distal portion of the inner wall of the collar for engaging the shoulder of the stem. The annular rim includes an undercut for catching the shoulder of the stem.

A pair of elongate notches are defined in the collar of the first piece for allowing temporary radial expansion of the distal portions of the collar when the outer section of the stem is inserted into the collar during assembly. This temporary radial expansion is reversed when the shoulder on the stem engages the undercut annular rim on the collar because of the resiliency of the plastic material. Advantageously, the notches facilitate removal of the molded adapter first piece from an injection mold—the temporary radial expansion of the collar permits the undercut collar to be snapped out of a mold with normal mold removal equipment, obviating use of expensive collapsible core pins in the mold.

Also provided is a separate second injection molded piece—a reinforcing ring having a diameter greater than the diameter of the outer diameter of the collar, and positionable over the stem prior to mating the collar with the stem. The reinforcing ring is slidably engagable with the collar after the annular rim on the collar engages with the shoulder on the stem, thereby resisting radial expansion of the collar during pressurization of the catheterization system. Advantageously, the reinforcing ring provides additional circumferential reinforcement about the collar, which contains the rotating "O" ring seals, and increases the overall pressure handling characteristics of the adapter.

A rotatable adapter constructed in accordance with the present invention can be quickly assembled by hand and is resistant to leakage at the seals under high fluid pressurization. Further, all pieces of the plastic adapter are inexpensive to mold and do not require collapsible core pins in the mold. Moreover, the elements forming the stem to which the adapter mates can be fabricated from rigid plastic or plastic of flexible tubing.

Accordingly, it is an object of the present invention to provide an improved rotating adapter for a catheterization system.

It is a further object of this invention to provide an adapter which is relatively inexpensive to manufacture.

It is a further object of this invention to provide an adapter that is quickly and inexpensively assembled by hand or by simple put and place robots.

It is a further object of this invention to provide an adapter that can withstand high fluid pressure in a catheterization system without leakage.

It is a further object of the present invention to provide a rotating adapter that is suitable for use with stems on rigid articles such as manifolds and the like, as well as on flexible tubing.

Other objects, features and advantages of the present invention will become apparent upon review of the following detailed description of embodiments of the invention, when taken in conjunction with the drawings and appended claims.

DETAILED DESCRIPTION OF THE DISCLOSED EMBODIMENT

Figures 1, 2:
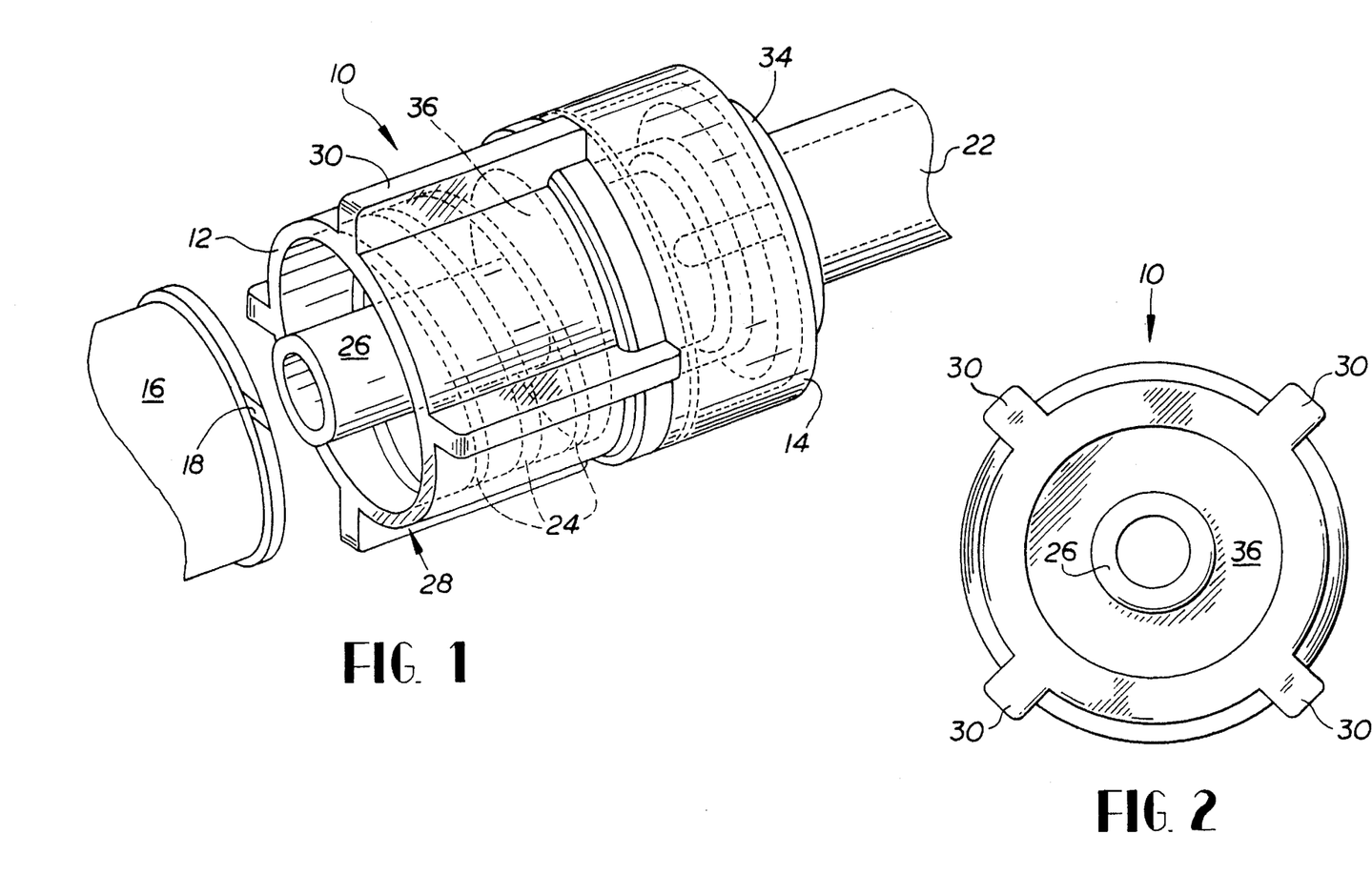
FIG. 1 is a front perspective view of a rotating adapter for a catheterization system constructed in accordance with the preferred embodiment of the present invention.
FIG. 2 is a front plan view of the preferred rotating adapter of FIG. 1.

Referring now to the drawings, in which like reference numerals correspond to like parts throughout the several views, FIG. 1 is a front perspective view of a rotating adapter 10 constructed in accordance with the preferred embodiment of the present invention, for a catheterization system. The preferred adapter 10 comprises a first piece 12 and a separate reinforcing ring 14. One end 28 of the adapter 10 is provided with grasping fins 30 and ANSI standard Luer threading 24 for a firm connection to a catheter stem 16 of a flexible catheter (not shown). Adapter 10 is itself connected to, and rotatable with respect to, a stem 22. Stem 22 may lead to a fluid distribution or collection manifold (not shown), flexible tubing, or any other high-pressure fluid carrying device. The reinforcing ring 14 is provided at the end 34 of the adapter 10 opposite the grasping end 28, for retaining and holding the adapter in a rotatable but pressure resistant manner on the stem 22.

Preferably, the catheter stem 16, first piece 12, reinforcing ring 14, and stem 22 are all made of injection molded plastic material for ease of manufacture and low cost. Polycarbonate plastic such as LEXAN HP-111, made by General Electric Company, is preferred as such material is widely available, extremely strong, low cost, easily injection molded, and relatively inexpensive. Clear plastics are preferred for medical applications so that the operator of the catheterization system can visually monitor fluids in the system and ensure that no air bubbles or other undesirable elements are present in the fluid flow.

In the preferred embodiment, the grasping end 28 includes standard male Luer connector threading 24 for connecting to standard female Luer connector threading 18 provided on the catheter stem 16. Fluid passes through the adapter 10 and into the catheter stem 16 through a fluid carrying inner tube 26 provided concentrically with the grasping end 28, interiorly of the adapter 10.

As can be seen in FIGS. 1 and 2, the grasping end 28 of the first piece 12 further comprises a plurality of elongate flanges or fins 30 on the outer surface of the end 28. The fins 30 provide means for grasping the adapter 10 while screwing the adapter onto a catheter stem 16, or for rotating an attached catheter relative to the stem 22.

The fins 30, four in the disclosed embodiment, are generally parallel and somewhat rectangular, with rounded ends, are diametrically opposed, and extend along a substantial portion of the adapter 10, but terminating at the reinforcing ring 14. Other means for grasping, such as a rough-surfaced grip pad, or more or fewer fins, or knurling, may also be utilized on the surface of the end 28 as grasping means.

As best seen in FIG. 2, a flat annular sealing surface 36 is provided on the interior of the grasping end 28 of the adapter, concentric with the inner tube 26, for mating with and sealing the interface between the adapter 10 and catheter stem 16 when threaded together. The tight fit provided by the Luer connection and flat sealing surface 36 frustrate axial rotation of adapter 10 relative to catheter stem 16.

Figure 3:
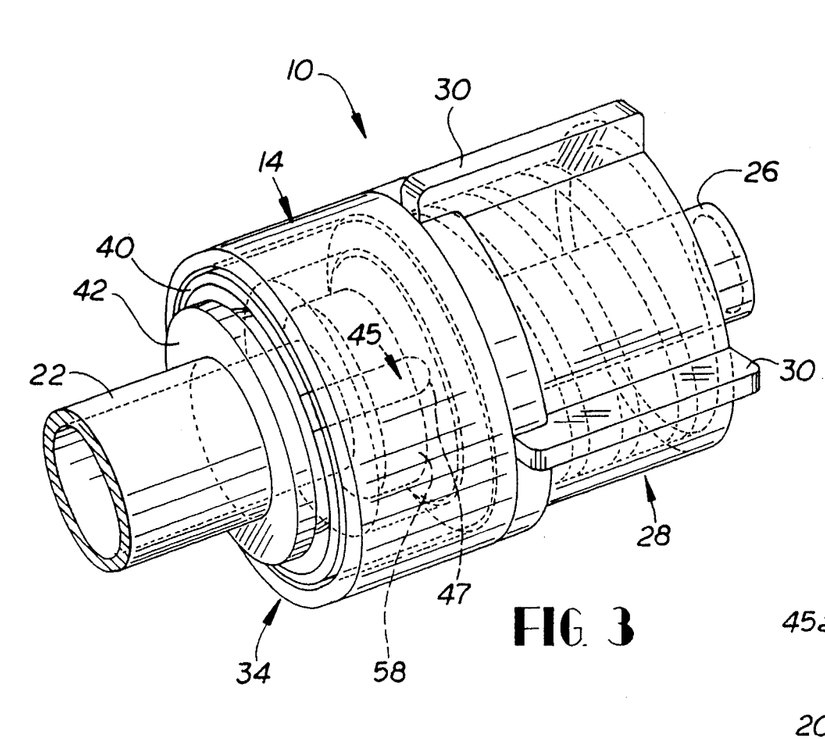
FIG. 3 is a rear perspective view of the preferred rotating adapter of FIG. 1, showing the manifold stem.
Figure 4:
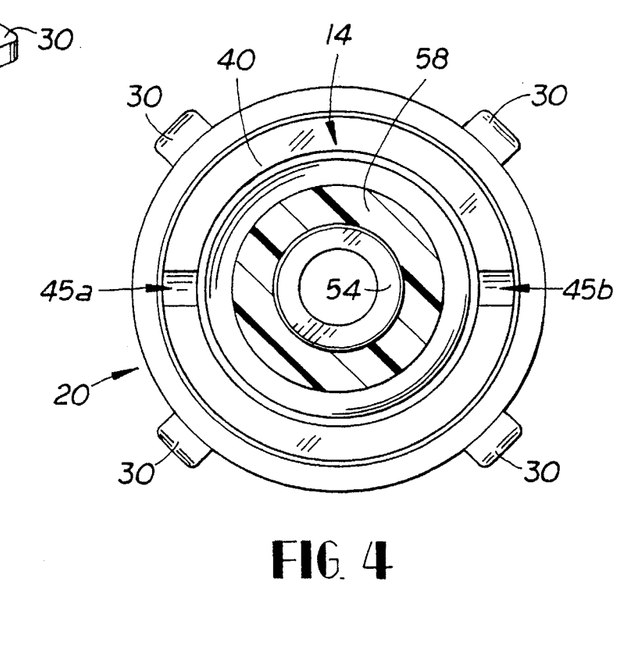
FIG. 4 is a rear plan view of the preferred rotating adapter of FIG. 1.

Referring now to FIG. 3, the first piece 12 of the preferred rotating adapter 10 further comprises, at its end 34 opposite the grasping end 28, an integrally molded collar 40 for rotatably attaching to the stem 22. The reinforcing ring 14 is concentric with and fits over the collar 40, to affix and reinforce the collar and hold it firmly to the stem 22.

Figure 6:
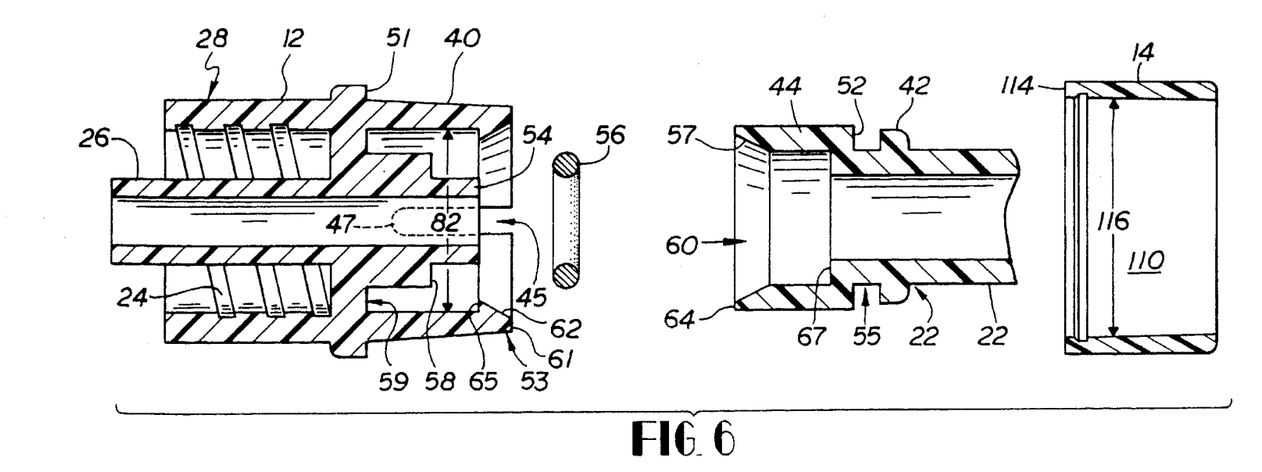
FIG. 6 is an exploded cross sectional view of the preferred rotating adapter of FIG. 1.
Figure 7:
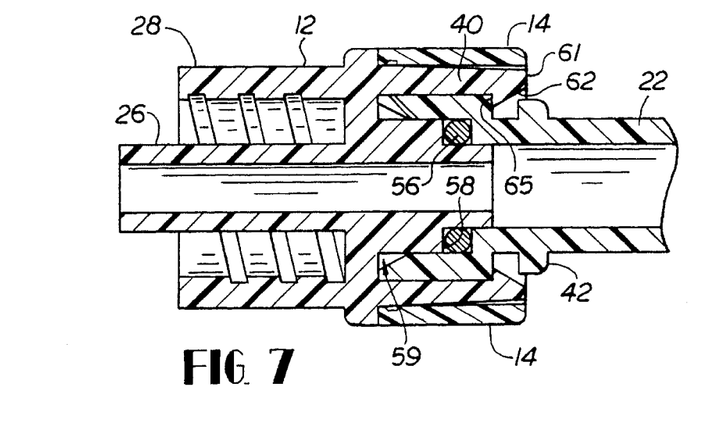
FIG. 7 is an assembled cross sectional view of the preferred rotating adapter of FIG. 1.

As best seen in FIGS. 3 and 7, the preferred stem 22 includes an annular flange 42 that protrudes out of the plane defined at the juncture of the collar 40 and reinforcing ring 14. As best seen in FIG. 6, the stem 22 further includes a shoulder 52 defined as one radially extending surface of an annular recess 55 provided between the annular flange 42 and an outer cylindrical section 44 of the stem. The outer cylindrical section 44 preferably has a diameter larger than the diameter of the remainder of the stem 22. The diameter of the cylindrical section 44, however, is selected to matingly engage with the interior of the collar 40 of the first piece 12.

The interior wall of the stem 22 defines, beginning at its leading edge 64, an inwardly tapered or frustoconical surface 57 leading into the cylindrical interior 60 of the stem, terminating at the annular sealing surface 67, where the diameter of the stem narrows to the diameter of the fluid carrying conduit of the stem. This taper 57 eases the process of assembly by serving as a guide to the edges of the plastic pieces as they are engaged.

As best seen in FIG. 6, inside the collar 40 of the first piece 12 is a shoulder 58 forming a sealing surface that contacts with an "O"-ring 56 disposed between the first piece 12 of the adapter and interior of the cylindrical section 44 of the stem 22. The collar 40 defines a concentric cylindrical ring, in between which the cylindrical section 44 of the stem 22 slides when mating to the adapter 10. Shoulder 58 protrudes diametrically outwardly from inner fluid carrying tube 54. A cylindrical recess 59 is provided interiorly of the collar 40 for receiving the cylindrical section 44 of the stem 22, and includes the shoulder 58.

It will now be understood that the interior walls of the cylindrical recess 59 define a first cylinder extending from the end or bottom of the recess toward the distal end 53 of the collar 40 to the shoulder 58, and a second, smaller diameter cylinder extending toward the distal end and terminating at the exit of the fluid carrying tube 54.

Also, the collar 40 includes a pair of oppositely disposed, longitudinally extending notches 45a, 45b, each having a rounded end 47, for allowing temporary expansion of the plastic material for removal of the piece 12 from the mold after forming and during assembly. Still referring to FIG. 6, the collar 40 is tapered slightly from its point of beginning at a ring abutment shoulder 51 radially inwardly to its distal end 53. The ring abutment shoulder 51 is provided at about the midpoint of the first piece 12, at the point of termination of the grasping fins 30. The inward taper permits slidable acceptance of the reinforcing ring 14 in a snug, friction fit.

The distal end 53 of the collar 40 includes an outer rim 61, an inwardly tapered frustoconical surface 62, and an undercut 65. The undercut 65 extends underneath the frustoconical surface 62, such that the inward termination point of the frustoconical surface has a small diameter than the diameter of the interior walls of the recess 59. The recess 59 and undercut 65 are provided for mating with and securing, in a snap fit, the shoulder 52 on the outer section 44 of the stem 22.

The ring 14 includes an interior tapering for making a snug fit with the collar 40 of the first piece 12. As best seen in FIG. 6, the inner diameter 116 of the ring 14 gradually decreases from its insertion end 114, which abuts against the abutment shoulder 51, to its outer end 118. Because the inner diameter 116 at end 118 of the reinforcer ring 14 is slightly smaller than the diameter at insertion end 114, the ring exerts inward radial pressure on the collar 40, thereby further compressing stem 22 onto gasket 56 and improving the sealing characteristics of the adapter 10. Further, reinforcing ring 14 prevents undercut 65 and shoulder 52 from being disengaged by unwanted expansion of collar 40. Therefore, the reinforcer ring 14 helps resist fluid leakage when positioned over the collar 40.

Figure 5:
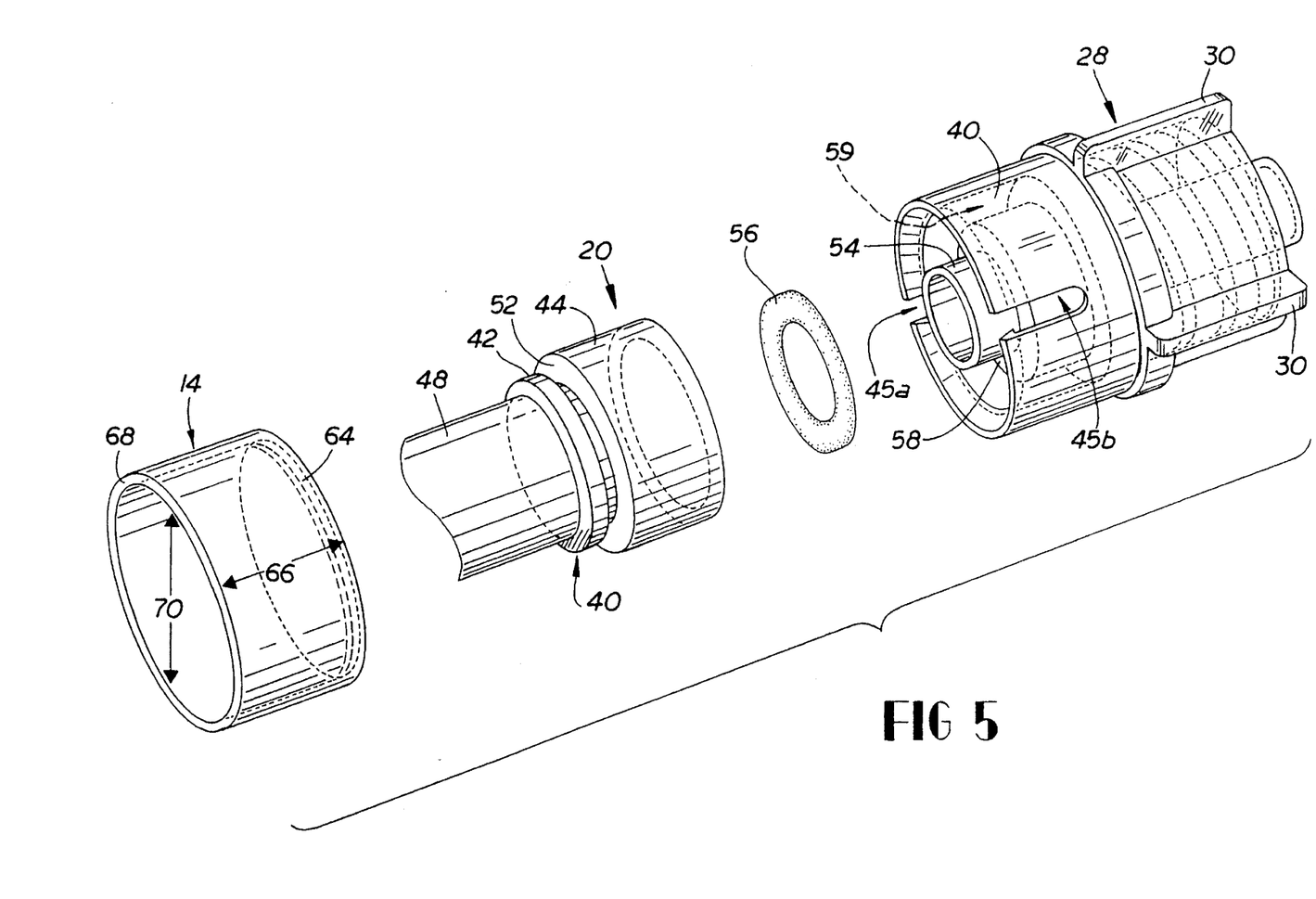
FIG. 5 is an exploded perspective view of the preferred rotating adapter of FIG. 1.

FIG. 5 shows the preferred rotating adapter 10 just prior to assembly, with the various pieces fined up for assembly. Assembly of the adapter first requires placing a rubber "O"-ring or gasket 56 on shoulder 58 in the first piece 12. The reinforcer ring 14 is placed over the stem 22 and slid axially away from the outer section 44 of the stem, where it rests until it is needed to complete the assembly.

Then, the outer section 44 of the stem 22 is inserted into the recess 59 of the collar 40. The gasket 56 will be compressed between an annular sealing surface 67 of the stem 22 and the shoulder 58, confined between the inner wall of stem 22 and the outer wall of an inner fluid carrying tube 54 where it opens into the void of the collar 40. The gasket 56 seals the fluid carrying joint between stem 22 and inner fluid carrying tube 54 once the assembly is complete, while permitting relative rotation between the first piece 12 and the manifold stem.

It will be recalled that the the outer section 44 of the stem 22 has a diameter smaller than the diameter of the void inside the collar 40. The stem 22 is pressed by hand assembly into this void until the shoulder 52 engages with the undercut 65 and snaps in place. The notches 45 allow temporary expansion of the material of the collar 40 until the pieces catch.

Note in FIG. 7 that when the outer section 44 of the stem 22 is mated with the collar 40, the end 64 of the stem abuts with the bottom of the recess 59, preventing undesirable axial compression of the "O"-ring 56.

After mating the stem 22 to the first piece 12, the reinforcing ring 14 is slid over the collar 40. The ring 14 is pushed over the collar 40 until it is snug and contacts with the ring abutment shoulder 51 on the first piece 12. Reinforcing ring 14 thereby secures the engagement between the stem 22 and the first piece 12, and completes the assembly of the adapter 10. The reinforcing ring confines the collar distal end 53 and prevents it from expanding under the influence of fluid pressure and possibly releasing the catch between the undercut 65 and shoulder 52. This provides means for reinforcing the snap fit connection against pressure or inadvertent removal.

As now completed, the grasping end 28 of the adapter 10 may be affixed to a catheter, and rotated with respect to the stem 22.

Figure 8:
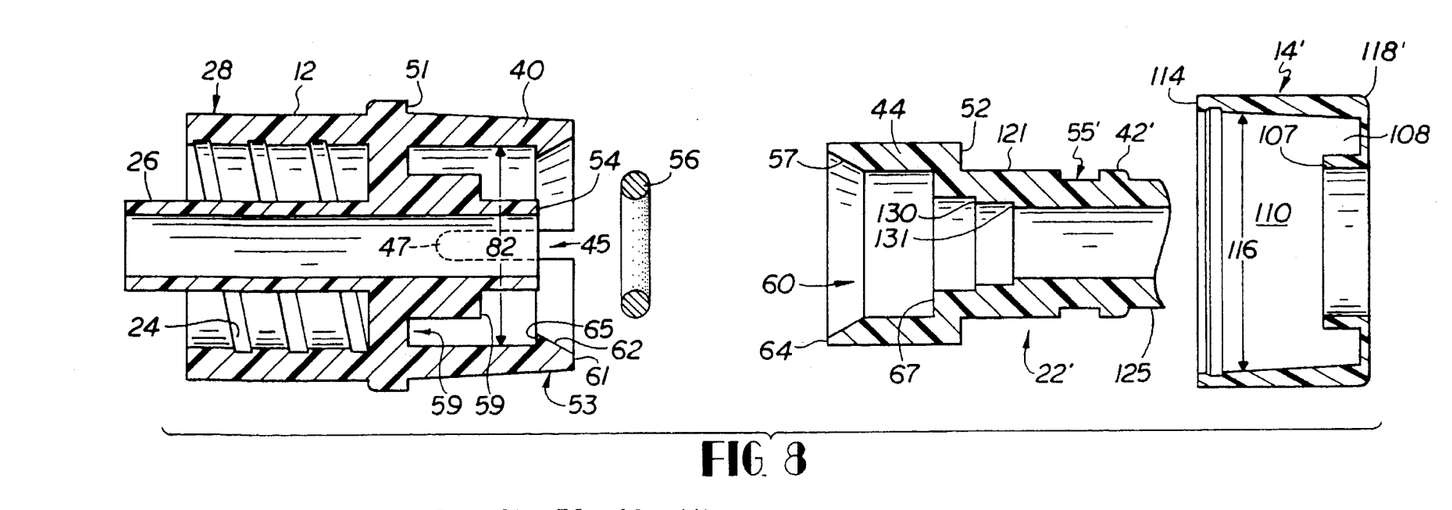
FIG. 8 is an exploded cross sectional view of another embodiment of a rotating adapter constructed in accordance with the present invention, for use on flexible tubing.
Figure 9:
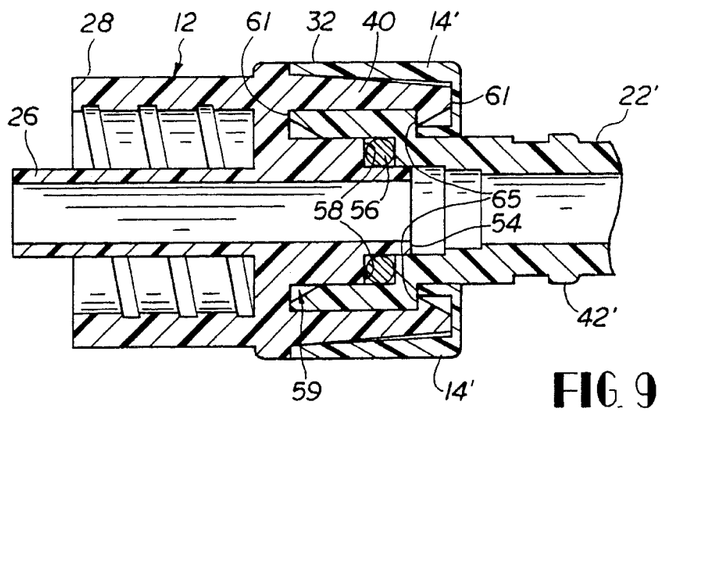
FIG. 9 is an assembled cross sectional view of the embodiment of the rotating adapter of FIG. 8.

FIGS. 8 and 9 show an alternative embodiment of a reinforcer ring 14' and a stem 22'. The alternative reinforcer ring 14' provides additional protection against undesirable release of the undercut 65. The alternative stem 22' is particularly suitable for use on flexible tubing such as 125.

A tubular flange 107 extends inwardly from the outer end 118' of the ring 14'. The tubular flange 107 has an inner diameter slightly greater than the outer diameter of the stem 22' at its portion 121 immediately adjacent to the cylindrical section 44, but smaller than the outer diameter of the outer cylindrical section 44. The portion 121 of the stem 22' is enlarged relative to the diameter of the tubing 125, so as to provide additional material and support against bending of the tubing where it forms the stem.

A recess 108 is formed between the inner wall of ring 14' and the outer wall of tubular flange 107. This recess is designed to fit over and matingly engage with the outer rim 61 of the collar 40 when the ring 14' is slidably disposed over the collar.

Stem 22' is further modified from the previous embodiment by providing an annular flange 42' disposed further away from the outer cylindrical section 44 which mates with collar 40. In the embodiment of FIG. 7, the flange 42 protrudes slightly from under the juncture of the collar 40. In FIG. 9, it will be seen that the flange 42' is further away from the collar 40. The diameter of the stem 22' at the portion 121 is reduced relative to the diameter of the outer section 44, but larger than the diameter of the flexible tube 125. The tubular flange 107 still easily slides over stem 22' and the portion 121.

The stem 22' further provides, on its interior, stepped interior diameter reductions at 130 and 131 to progressively reduce the interior fluid-carrying diameter leading into the tubing 125.

A recess 55' defined between the annular flange 42' and the enlarged portion 121 of the stem 22' provides a catch for extracting the stem from molds. This obviates the need for a collapsible core pin (not shown) when molding stem 22'. Those skilled in the art will recognize that annular flange 42' (or 42) may be located at many positions along stem 22'.

As shown in FIG. 9 with the alternative embodiment of reinforcer ring 14', the recess 108 of the ring matingly engages and surrounds the outer rim 61 of the collar 40, yet further still resisting outward radial expansion of the collar 40 and possible release of the undercut 65 from its capture of the outer section 44 of the stem 22'. Further, ring 14' is secured in position by friction between the inner wall of tubular flange 107 and the portion 121 of the stem 22'. This further locks the ring 14' and the collar 40 in position and increases the pressure resistive characteristics of the adapter 10, while maintaining easy assembly of adapter by hand.

It will be understood and appreciated that the entire adapter 10 may be assembled with unskilled manual labor, or with a simple put-and-place type robot, without use of any tools or heating means for permanently deforming any plastic parts. All that is required, simply stated, is to slip the reinforcer ring over the manifold stem, insert an "O"-ring, mate the first piece to the manifold stem until the undercut snaps into place, and slide the reinforcer ring into position over the collar until it fits snugly. Alternatively, a drop of glue may be deposited on the collar 40 prior to positioning the reinforcer ring 14, for additional strength in holding the ring in place and resisting pressure. Preferably, a UV cured cement such as Loc-tite 399 low viscosity UV curing PVC adhesive is used, but other types of glue such as methyl acrylate are also suitable.

The reinforcer rings 14, 14' provided in the present invention provide for substantially improved resistance to pressure than in prior art rotatable adapters. An adapter 10 constructed in accordance with the present invention can withstand fluid pressures of up to approximately 400 pounds per square inch (psi) before leakage occurs. However, when reinforcer ring 14, 14' is placed over collar 40, the catheterization system can withstand much higher fluid pressures up to approximately 1,000 psi. Use of glue on the collar 40 before sliding reinforcing ring 14, 14' over the collar is believed to increase the fluid pressure resistance to the point at which the preferred polycarbonate plastic is susceptible to failure. Due to the combined wall thickness of the reinforcer ring 14 and collar 40, which is about 0.070 inches, an adapter made in accordance with the present invention holds pressure up to approximately 1,800 psi or more.

It should also be noted that notches 45 contribute to the low cost of manufacture of the preferred adapter by eliminating the need for a collapsible pin core injection mold for the first piece 12. Collapsible pin cores are structures or protrusions provided on the interior of injection molds which can moved or collapsed inside the mold to facilitate removal of molded articles. Those skilled in the art of plastic injection molding will recognize that the features such as the undercut 65 in molded plastic articles typically require use of such collapsible pin cores in the mold.

The notches 45, which allow temporary expansion of the distal end 53 of the collar 40 when the collar is engaged with the stem 22, similarly allow easy removal of the first piece 12 from its injection mold. The notches allow temporary expansion of the distal end 53 of the collar 40 radially outwardly to facilitate removal of the undercut 65 from portions or protrusions on the interior of the plastic mold that are provided in the mold to form the undercut. Further, annular flange 42 or 42' provides a catching mechanism which can be used to pull stem 22 from the mold, again negating the need for a collapsible core pin. Therefore, all plastic pieces of the preferred embodiment of the present invention may be molded without a collapsible core pin.

While this invention is described in detail with particular reference to the preferred embodiment thereof, it will be understood that other variations and modifications can be made without departing from the spirit and scope of the invention as defined in the appended claims.

What is claimed is:

1. In a catheterization system including a stem having at one end an outer section with a diameter greater than the diameter of an inner section of the stem, and an outer shoulder formed at the juncture of the outer section and the inner section, a rotating adapter for rotatably connecting to the stem, the combination thereof comprising:

a collar;

an inner fluid-carrying tube extending within said collar;

an inner annular shoulder protruding diametrically outwardly from said inner fluid-carrying tube;

an O-ring disposed between said inner annular shoulder and the interior of the stem, said O-ring being compressed between said inner annular shoulder and the stem when the stem and said collar are mated;

expansion means on said collar for enabling temporary radial expansion of said collar to permit the stem to be inserted into said collar and to retract said radial expansion after the stem has been inserted into said collar;

capture means on said collar for securely capturing said collar on the stem; and reinforcer means for inhibiting unwanted radial expansion of said collar after the stem and said collar have been mated.

2. The combination of claim 1, wherein said expansion means comprises at least one notch formed into said collar, said notch facilitating outward radial expansion of said collar during mating of said collar to the stem.

3. The combination of claim 2, wherein said expansion means comprises two notches located diametrically opposite each other on said collar.

4. The combination of claim 1, wherein said capture means comprises an undercut in the material of said collar, said undercut engaging the outer shoulder of the stem when said collar and stem are mated.

5. The combination of claim 1, wherein said capture means comprises an inwardly protruding annular rim on said collar, said annular rim engaging the outer shoulder on the stem when said collar and the stem are mated.

6. The combination of claim 1, wherein said reinforcer means comprises a tubular reinforcer ring slidably interfitting with said collar to prevent outward radial motion of said expansion means.

7. The combination of claim 6, wherein said reinforcer ring has a tapered interior diameter so as to permit one end of said reinforcer ring to engage with said expansion means and progressively restrict said expansion means when placed on said collar.

8. The combination of claim 6, including a tubular flange extending inwardly from one end of said reinforcer ring, said tubular flange slidably interfitting with the stem, wherein a recess is formed between the outer wall of said tubular flange and the inner wall of said reinforcer ring, said recess engaging said collar when the stem and said collar are mated and said reinforcer ring is affixed over said collar.

9. Apparatus for a catheterization system for rotatably connecting to a stem, the stem having at one end an outer section with a diameter greater than the diameter of an inner section of the stem, and an outer shoulder defined at the juncture of the outer section and the inner section, comprising in combination therewith:
   a cylindrical collar for mating with the stem, said collar having an inner diameter greater than the outer diameter of the outer section of the stem, and an undercut on the inner wall of said collar for engaging the outer shoulder on the stem;
   an inner fluid-carrying tube extending within said collar;
   an inner annular shoulder protruding diametrically outwardly from said inner fluid-carrying tube;
   an O-ring disposed between said inner annular shoulder and the interior of the stem, said O-ring being compressed between said inner annular shoulder and the stem when the stem and said collar are mated; and
   at least one notch in said collar for enabling temporary radial expansion of said collar to allow the outer section of the stem to be inserted into said collar and said undercut to engage the outer shoulder.

10. Apparatus of claim 9, wherein said undercut comprises an annular rim located on the inner wall of said collar.

11. Apparatus of claim 10, wherein the diameter of said annular rim gradually decreases as said annular rim extends into the interior void of said collar, forming a step defined between said annular rim and the inner wall of said collar, which step engages the outer shoulder on the stem when the stem and said collar are mated.

12. Apparatus of claim 9, further comprising at least one fin on the exterior of said adapter to aid in grasping said adapter.

13. Apparatus of claim 9, wherein the end of said adapter opposite the end mated to the stem is threaded on its interior for mating with a second stem.

14. A rotating adapter for a catheterization system for rotatably connecting to a stem, the stem having at one end an outer section with a diameter greater than the diameter of an inner section of the stem, and a outer shoulder formed at the juncture of the outer section and the inner the combination with said stem, comprising:
   a cylindrical collar for mating with the stem, said collar having an inner diameter for slidably receiving the outer section of the stem;
   an inner fluid-carrying tube extending within said collar;
   an inner annular shoulder protruding diametrically outwardly from said inner fluid-carrying tube;
   an O-ring disposed between said inner annular shoulder and the interior of the stem, said O-ring being compressed between said inner annular shoulder and the stem when the stem and said collar are mated;
   a protrusion on the inner wall of said collar, said protrusion being positioned to engage the outer shoulder when the stem and said collar are mated;
   at least one notch in said collar for enabling temporary radial expansion of said collar to allow the outer section of the stem to be inserted into said collar, said temporary radial expansion being reversed when said protrusion on said collar engages the outer shoulder on the stem; and
   a reinforcer ring slidably affixable about said collar after the stem is inserted into said collar, thereby resisting expansion of said collar during pressurization of the catheterization system.

15. The combination of claim 14, wherein said protrusion comprises an annular rim located on an outermost portion of the inner wall of said collar.

16. The combination of claim 15, wherein the diameter of said annular rim gradually decreases as said rim extends inwardly into the interior void of said collar, forming a step between said annular rim and the inner wall of said collar, which step engages the outer shoulder on the stem when the stem and said collar are mated.

17. The combination of claim 14, including at least one grasping fin on the exterior of said adapter.

18. The combination of claim 14, wherein an end of said adapter opposite said collar is threaded on its interior for mating with a second stem.

19. The combination of claim 14, comprising at least two notches located diametrically opposite each other on said collar.

20. The combination of claim 14, wherein said reinforcing ring has a diameter at a first end greater than the outer diameter of said collar, thereby permitting said first end of said reinforcing ring to slidably interfit with said collar, and wherein said diameter of said reinforcing ring tapers at a second end to a diameter less than the outer diameter of said collar, thereby enabling said second end of said reinforcing ring to radially constrict said collar when disposed over said collar.

21. The combination of claim 14, including a tubular flange extending inwardly from one end of said reinforcing ring, said tubular flange slidably interfitting with the stem, wherein a recess is formed between the outer wall of said tubular flange and the inner wall of said reinforcer ring, said recess engaging said collar when the stem and said collar are mated and said reinforcing ring is affixed over said collar.

22. Apparatus for a chatheterization system for providing rotatable connection to a stem, the stem having at one end an outer section with a diameter greater than the diameter of an inner section of the stem, and an outer shoulder formed at the juncture of the outer section and the inner section, in combination with said stem, comprising:

a cylindrical collar for mating with the stem, said collar having an inner diameter for slidably receiving the outer section of the stem, and a protrusion on the inner wall of said collar for engaging the outer shoulder on the stem;

at least one notch in said collar for enabling temporary radial expansion of said collar to allow the outer section of the stem to be inserted into said collar, said temporary radial expansion being reversed when said protrusion on said collar engages the shoulder on the stem; and a reinforcer ring slidably affixable about said collar after the stem is inserted into said collar, including a tubular flange extending inwardly from one end of said reinforcing ring, said tubular flange slidably interfitting with the stem, wherein a recess is formed between the outer wall of said tubular flange and the inner wall of said reinforcer ring, said recess engaging the outer end of said collar that extends over the outer shoulder on the stem when the stem and said collar are mated and said reinforcer ring is affixed over said collar.

23. A rotating adapter for a catheterization system comprising:

a stem having an outer section and an inner section, the diameter of said outer section being greater than the diameter of said inner section, thereby defining a outer shoulder at the juncture of said outer section and said inner section;

at least one fin positioned on said adapter for grasping;

a collar on one end of said adapter for mating with said stem, said collar including an annular rim around an outermost portion of the inner wall of said collar for engaging said outer shoulder of the stem;

an inner fluid-carrying tube extending within said collar;

an inner annular shoulder protruding diametrically outwardly from said inner fluid-carrying tube;

an annular gasket disposed between said inner annular shoulder and the interior of said stem, said annular gasket being compressed between said inner annular shoulder and said stem when said stem and said collar are mated;

at least one notch defined in said collar for allowing temporary radial expansion of said collar when said outer section of said stem is inserted into said collar during assembly, said temporary radial expansion being reversed when said shoulder on said stem engages said annular rim on said collar;

a reinforcer ring having a diameter slightly greater than the outer diameter of said collar, and positionable over said stem prior to mating said rotating adapter and stem;

said reinforcer ring including a tubular flange extending inwardly from one end of said reinforcer ring, said tubular flange slidably interfitting with said stem, and wherein a recess is formed between the outer wall of said tubular flange and the inner wall of said reinforcer ring, said recess engaging the outer end of said collar when said stem and said collar are mated and said reinforcer ring is affixed over said collar;

said reinforcer ring being slidably engagable with said collar after said annular rim on said collar engages said outer shoulder on said stem, thereby resisting radial expansion of said collar during pressurization of said catheterization system; and a second collar on said adapter for engaging with a second stem.

24. A method of assembling a rotating adapter for a catheterization system, to rotatably connect the adapter to a stem, comprising the steps of:

providing a tubular stem having at one end an outer section with a diameter greater than the diameter of a second section of the stem, and an outer shoulder defined at the juncture of the sections;

providing an adapter having at one end a collar for slidably engaging with the stem, said collar including a protrusion on the inner wall of the collar for engaging the outer shoulder of the stem;

providing a reinforcer ring for slidably interfitting with the collar, said reinforcer ring including a tubular flange extending inwardly from one end of said reinforcer ring, said tubular flange slidably interfitting with the outer section of the stem, and wherein a recess is formed between the outer wall of said tubular flange and the inner wall of said reinforcer ring;

inserting the reinforcer ring over the stem;

mating the outer section of the stem with the collar until the protrusion on the inner wall of the collar engages with the outer shoulder of the tubular stem;

sliding the reinforcer ring over the collar and outer section of the stem to confine the collar and resist radial expansion of the collar under pressure; and providing at least one notch in the collar for allowing temporary radial expansion of the collar to permit the outer section of the stem to be slidably interfitted with the collar during mating of said adapter and the stem.

25. The method of claim 24, wherein the collar includes a frustoconical surface extending radially inwardly from the edge of the collar that mates with the stem to terminate at the protrusion on the inner wall of the collar, and further comprising the steps of:

engaging the frustoconical surface of the collar with the outer section of the stem to cause temporary radial expansion of the collar and receive the outer section of the stem; and moving the outer section of the stem into engagement with the frustoconical surface until the protrusion on the inner wall of the collar passes over and engages the outer shoulder of the stem.

26. In a catheterization system including a stem having at one end an outer section with a diameter greater than the diameter of an inner section of the stem, and a outer shoulder formed at the juncture of the outer section and the inner section, a rotating adapter for rotatably connecting to the stem, comprising in combination:

expansion means in a collar on a first end of said adapter for enabling temporary radial expansion of said adapter to permit the stem to be inserted into said adapter and to retract said radial expansion after the stem has been inserted into said adapter;

capture means on said first end of said adapter for securely capturing said adapter on the stem;

a tubular reinforcer ring slidably interfitting with said adapter to prevent outward radial motion of said expansion means; and a tubular flange extending inwardly from one end of said reinforcer ring, said tubular flange slidably interfitting with the stem, wherein a recess is formed between the outer wall of said tubular flange and the inner wall of said reinforcer ring, said recess engaging the end of said collar that extends over the outer shoulder on the stem when the stem and said collar are mated and said reinforcer ring is affixed over said collar.

27. Apparatus for a catheterization system for providing rotatable connection to a stem, the stem having at one end an outer section with a diameter greater than the diameter of an inner section of the stem, and a outer shoulder defined at the juncture of the outer section and the inner section, in combination with said stem comprising:

a cylindrical collar at a first end of said adapter for mating with the stem, said collar having an inner diameter greater than the outer diameter of the outer section of the stem, and an annular rim located on the inner wall of said collar for engaging the outer shoulder on the stem;

an inner fluid-carrying tube extending within said collar;

an inner annular shoulder protruding diametrically outwardly from said inner fluid-carrying tube;

an O-ring disposed between said inner annular shoulder and the interior of the stem, said O-ring being compressed between said inner annular shoulder and the stem when the stem and said collar are mated; and at least one notch in said collar for enabling temporary radial expansion of said collar to allow the outer section of the stem to be inserted into said collar and said annular rim to engage said outer shoulder.

28. A rotatable adapter for a catheterization system for rotatably connecting to a stem, the stem having at one end an outer section with a diameter greater than the diameter of an inner section of the stem, and a outer shoulder defined at the juncture of the outer section and the inner section, comprising in combination:

a cylindrical collar at a first end of said adapter for mating with the stem, said collar having an inner diameter greater than the outer diameter of the outer section of the stem, and an annular rim located on the inner wall of said collar for engaging the outer shoulder on the stem, wherein the diameter of said annular rim is greater at a distal end of said collar, and the diameter of said annular rim gradually decreases as said annular rim extends into the interior void of said collar, forming a step between the innermost portion of said annular rim and the inner wall of said collar, which step engages the outer shoulder on the stem when the stem and said collar are mated;

an inner fluid-carrying tube extending within said collar;

an inner annular shoulder protruding diametrically outwardly from said inner fluid-carrying tube;

an O-ring disposed between said inner annular shoulder and the interior of the stem, said O-ring being compressed between said inner annular shoulder and the stem when the stem and said collar are mated; and at least one notch in said collar for enabling temporary radial expansion of said collar to allow the outer section of the stem to be inserted into said collar and said annular rim to engage said outer shoulder.

29. A rotating adapter for a catheterization system for rotatably connecting to a stem, the stem having at one end an outer section with a diameter greater than the diameter of an inner section of the stem, and a outer shoulder formed at the juncture of the outer section and the inner section, comprising in combination:

a cylindrical collar at a first end of said adapter for mating with the stem, said collar having an inner diameter for slidably receiving the outer section of the stem;

an inner fluid-carrying tube extending within said collar;

an inner annular shoulder protruding diametrically outwardly from said inner fluid-carrying robe;

an O-ring disposed between said inner annular shoulder and the interior of the stem, said O-ring being compressed between said inner annular shoulder and the stem when the stem and said collar are mated;

a protrusion on the inner wall of said collar, said protrusion being positioned to engage the outer shoulder when the stem and said collar are mated;

at least one notch in said collar for enabling temporary radial expansion of said collar to allow the outer section of the stem to be inserted into said collar, said temporary radial expansion being reversed when said protrusion on said collar engages the outer shoulder on the stem;

a reinforcer ring slidably affixable about said collar after the stem is inserted into said collar, thereby resisting expansion of said collar during pressurization of the catheterization system; and a tubular flange extending inwardly from one end of said reinforcer ring, said tubular flange slidably interfitting with the stem, wherein a recess is formed between the outer wall of said tubular flange and the inner wall of said reinforcer ring, said recess engaging the outer end of said collar that extends over the outer shoulder on the stem when the stem and said collar are mated and said reinforcer ring is affixed over said collar.

30. A rotating adapter for a catheterization system for rotatably connecting to a stem, the stem having at one end an outer section with a diameter greater than the diameter of an inner section of the stem, and a outer shoulder formed at the juncture of the outer section and the inner section, comprising in combination:

a collar for mating with the stem, said collar having two ends including an opening at a first end, said collar having an inner diameter greater than the outer diameter of the outer section of the stem;

expansion means in said collar for allowing temporary radial expansion of said collar to allow the outer section of the stem to be inserted into said collar;

said collar including a frustoconical surface defined at the first end of said collar and extending inwardly into an interior void of said collar, said frustoconical surface for engaging with the outer section of the stem, said frustoconical surface causing said expansion means to expand the diameter of said collar when the outer section of the stem is engaged with said frustoconical surface during insertion of the outer section of the stem into said collar;

a reinforcer ring around said collar for resisting radial expansion of said collar;

a tubular flange extending inwardly from one end of said reinforcer ring, said tubular flange slidably interfitting with the stem, and wherein a recess is formed between the outer wall of said tubular flange and the inner wall of said reinforcer ring, said recess engaging the outer end of said collar that extends over the outer shoulder on the stem when the stem and said collar are mated and said reinforcer ring is affixed over said collar.

* * * * *

UNITED STATES PATENT AND TRADEMARK OFFICE
CERTIFICATE OF CORRECTION

PATENT NO. : 5,509,911

DATED : April 23, 1996

INVENTOR(S) : Joseph R. Cottone, Sr.

Anthony J. Cottone

It is certified that error appears in the above-identified patent and that said Letters Patent are hereby corrected as shown below:

In column 6, line 25, change "fined" to --lined--.

Col. 10, claim 14, line 5, after "and the inner" insert --section--.

In claim 22, line 1, change "chatheterization" to --catheterization--.

In claim 29, column 14, line 6, change "robe" to --tube--.

Signed and Sealed this

Twenty-third Day of July, 1996

Attest:

BRUCE LEHMAN

Attesting Officer

Commissioner of Patents and Trademarks